United States Patent
Chaja et al.

(10) Patent No.: US 11,744,495 B2
(45) Date of Patent: Sep. 5, 2023

(54) METHOD FOR OBJECTIVELY TRACKING AND ANALYZING THE SOCIAL AND EMOTIONAL ACTIVITY OF A PATIENT

(71) Applicant: From Zero, LLC, Northridge, CA (US)

(72) Inventors: Kevin Chaja, Northridge, CA (US); Natasha Chaja, Northridge, CA (US)

(73) Assignee: From Zero, LLC, Northridge, CA (US)

( * ) Notice: Subject to any disclaimer, the term of this patent is extended or adjusted under 35 U.S.C. 154(b) by 8 days.

(21) Appl. No.: 17/651,795

(22) Filed: Feb. 19, 2022

(65) Prior Publication Data
US 2022/0167896 A1 Jun. 2, 2022

Related U.S. Application Data

(63) Continuation of application No. 16/531,049, filed on Aug. 3, 2019, now Pat. No. 11,253,181.
(Continued)

(51) Int. Cl.
*A61B 5/16* (2006.01)
*G06F 3/01* (2006.01)
(Continued)

(52) U.S. Cl.
CPC .............. *A61B 5/165* (2013.01); *G06F 3/012* (2013.01); *G06F 3/04883* (2013.01);
(Continued)

(58) Field of Classification Search
CPC ....... A61B 5/165; A61B 5/7445; G06F 3/012; G06F 3/04883; G06F 9/542;
(Continued)

(56) References Cited

U.S. PATENT DOCUMENTS 8,810,657 B1 * 8/2014 Slavin .................... H04N 7/183
348/156
9,176,325 B2 11/2015 Lyons
(Continued)

FOREIGN PATENT DOCUMENTS

WO 2018082782 A1 5/2018
WO WO-2018082782 A1 * 5/2018 .............. G06F 3/011

*Primary Examiner* — Said Broome
*Assistant Examiner* — Donna J. Ricks
(74) *Attorney, Agent, or Firm* — UltimatEdge IP Law Group, P.C.; Dean G. Stathakis

(57) ABSTRACT

A method and system for objectively tracking and analyzing the social and emotional activity of a patient using an augmented reality computing device is provided. A patient is permitted to manually manipulate a target object in the physical world while viewing an augmented version showing a unique animated character representing either an abstract language, emotions, or social skills, depending on the module. The present system tracks and records the active face and the time spent on the active face, where the active face is the face upon which the patient's focus is automatically estimated, through calculation, to be trained upon. An observer views the session, the data recorded, and an automatically generated graphical representation of the data, which permits the observer to speak to patient regarding the character or scene rendered on the face which is determined to be the active face, helping the student engage in the session.

17 Claims, 5 Drawing Sheets

Related U.S. Application Data

(60) Provisional application No. 62/714,365, filed on Aug. 3, 2018.

(51) Int. Cl.
*G06F 3/04883* (2022.01)
*G06T 19/00* (2011.01)
*G06F 9/54* (2006.01)
*G06T 7/00* (2017.01)

(52) U.S. Cl.
CPC ............ *G06F 9/542* (2013.01); *G06T 7/0014* (2013.01); *G06T 19/006* (2013.01); *G06F 2203/011* (2013.01); *G06T 2207/30201* (2013.01)

(58) Field of Classification Search
CPC .. G06F 2203/011; G06F 3/011; G06T 7/0014; G06T 19/006; G06T 2207/30201
See application file for complete search history.

(56) References Cited

U.S. PATENT DOCUMENTS

| | | |
|---|---|---|
| D751,072 S | 3/2016 | Lyons |
| 9,274,340 B2 | 3/2016 | Lyons |
| D755,789 S | 5/2016 | Lyons |
| 9,377,626 B2 | 6/2016 | Lyons |
| D760,701 S | 7/2016 | Lyons |
| 9,599,824 B2 | 3/2017 | Lyons |
| 9,695,553 B2 | 3/2017 | Kendrick |
| 10,302,951 B2 | 5/2019 | Lyons |
| 2006/0119601 A1* | 6/2006 | Finlayson ............... G06T 15/20 345/427 |
| 2016/0198996 A1* | 7/2016 | Dullen ................. A61B 5/4824 600/301 |
| 2016/0323324 A1* | 11/2016 | Knotts .................. H04L 65/104 |
| 2018/0032682 A1* | 2/2018 | Donalds ................ G16H 40/67 |
| 2018/0226158 A1* | 8/2018 | Fish ..................... G16H 30/20 |
| 2019/0265488 A1 | 8/2019 | Lyons |
| 2019/0318504 A1* | 10/2019 | Kozaki ................. G06T 19/006 |
| 2020/0020024 A1* | 1/2020 | Lyons .................... G06T 19/20 |
| 2020/0043242 A1* | 2/2020 | Hu ....................... G02B 27/017 |

\* cited by examiner

METHOD FOR OBJECTIVELY TRACKING AND ANALYZING THE SOCIAL AND EMOTIONAL ACTIVITY OF A PATIENT

This 35 U.S.C. § 111 patent application is a continuation that claims the benefit of priority and is entitled to the filing date pursuant to 35 U.S.C. § 120 of U.S. Non-Provisional patent application Ser. No. 16/531,049, filed Aug. 3, 2019, a 35 U.S.C. § 111 patent application which claims the benefit of priority and the filing date pursuant to 35 U.S.C. § 119(e) to U.S. Provisional Patent Application 62/714,365, filed Aug. 3, 2018, the entire content of each of which is hereby incorporated by reference in its entirety.

BACKGROUND

The subject of this patent application relates generally to systems and methods for use in social skills, language, and emotion training, and more particularly to systems and methods for utilizing objects configured for display of augmented reality images to aid in this training.

By way of background, children psychologists, marriage/family therapists, behavior specialists, speech/language pathologists, occupational therapists, parents, teachers, and other mental health support providers often have difficulty in opening a dialog with children with autism or other social/emotional needs and sustaining meaningful engagement with the child. The most effective method to engage such students currently used is a box of crayons and paper. A facilitator simply asks the student to drawn what they are feeling and then asks the student what the drawing means. However, it often takes several minutes to engage a child (for example, an average of about five minutes in one study), which is a substantial amount of time in a short 30-minute session. In addition, the engagement may only last a short time (for example, on average of about ten minutes, in the same study). The objective of many of these sessions is to guide the child in correctly identifying thoughts and feelings and engaging in a conversation about the child's own experience that elicited the those thoughts and feelings. The goal is to build the child's emotional, language, and social skills so that the child can initiate and maintain appropriate social interactions.

What is needed are tools to aid engaging the child in therapy, screenings, or other situations where it is desired that the child communicate and engage within the session. What is also needed are tools to efficiently and effectively teach the child social skills, language skills, and emotional skills. Aspects of the present invention fulfill these needs and provide further related advantages as described in the following summary.

SUMMARY

Aspects of the present invention teach certain benefits in construction and use which give rise to the exemplary advantages described below.

The present invention solves the problems described above by providing a method for objectively tracking and analyzing the social and emotional activity of a patient using a computing device. In one embodiment, a method disclosed herein comprises the steps of: implementing an augmented reality tracking application in memory on the computing device; upon the augmented tracking application being initialized on the computing device, detecting by at least one camera a target object manipulated by the patient, the target object comprising at least a first face and a second face, a first fiducial marker positioned on the first face and a second fiducial marker positioned on the second face; detecting at least one of the first fiducial marker and the second fiducial marker; displaying on a screen of the computing device an augmented image overlaid on the target object, the augmented image comprising a first image associated with the first fiducial marker and a second image associated with the second fiducial marker; detecting a position and a rotation relative to the camera of the target object for each point in time for which a data point is collected; calculating a coordinate data set of the target object based on the position and the rotation detected; determining an active face for each point in time using the coordinate data set and a parameter indicative of the patient focusing attention on one of the first image and the second image, wherein the active face can be dynamically assigned to one of either the first face or the second face at each point in time; and storing as a data set the data point for each point in time, the data point comprising the coordinate data set, the active face, and a time.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

Figure 1:
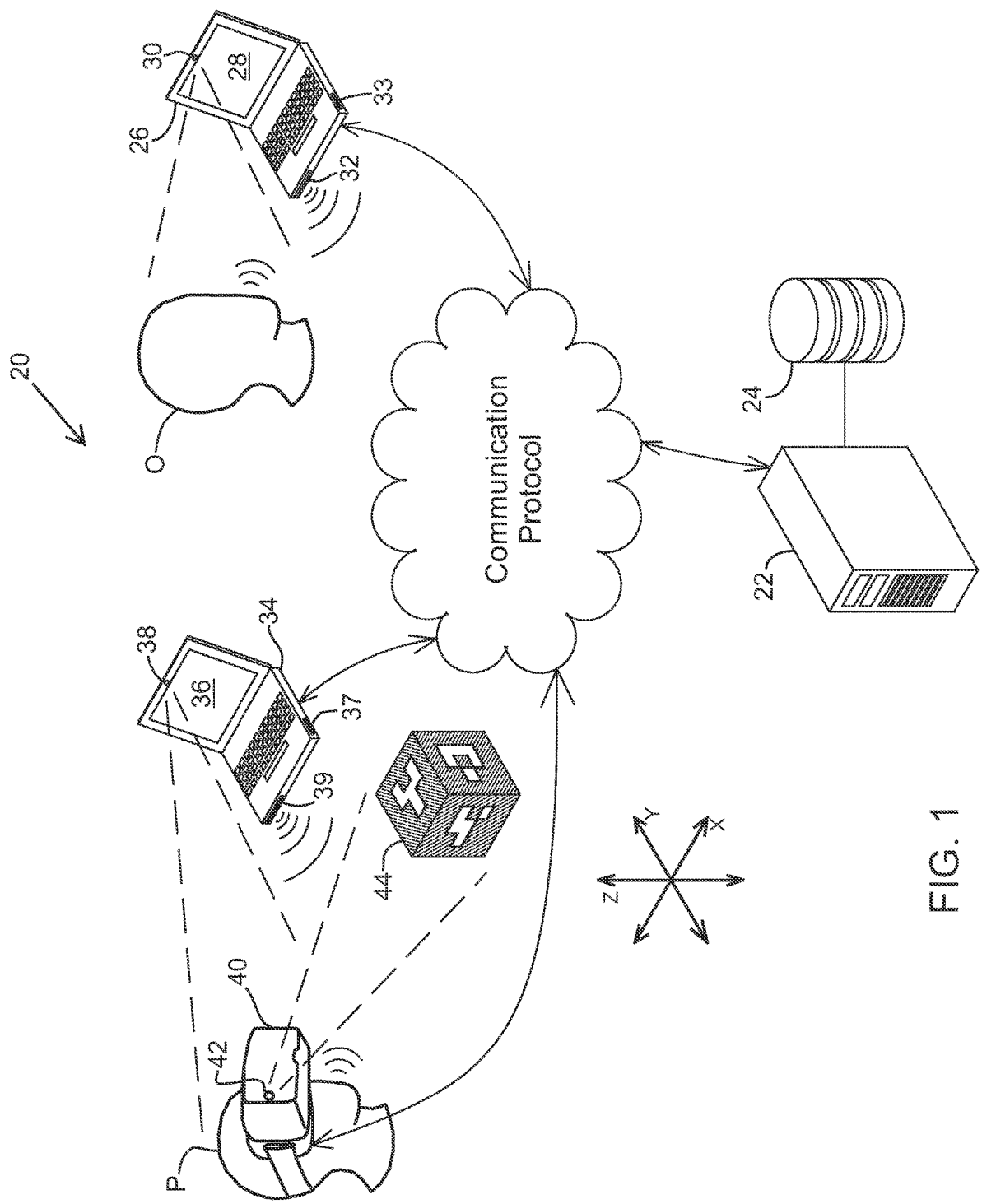
FIG. 1 is a simplified schematic view of an exemplary system for facilitating an augmented reality therapy session using one or more computing devices, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

The detailed descriptions set forth below in connection with the appended drawings are intended as a description of embodiments of the invention, and is not intended to represent the only forms in which the present invention may be constructed and/or utilized. The descriptions set forth the structure and the sequence of steps for constructing and operating the invention in connection with the illustrated embodiments. It is to be understood, however, that the same or equivalent structures and steps may be accomplished by different embodiments that are also intended to be encompassed within the spirit and scope of the invention.

The present system and method provides a tool for increasing the speed of engagement and length of engagement with a child or other patient in therapy. Further, the present system and method teach the child to effectively communicate emotions and to discuss events being displayed, which help to teach the child social skills, language skills, and emotional skills.

Computer networks are well known in the art, often having one or more client computers and one or more servers, on which any of the methods and systems of various disclosed embodiments may be implemented. In particular the computer system, or server in this example, may represent any of the computer systems and physical components necessary to perform the computerized methods discussed in connection with the present figures and, in particular, may represent a server (cloud, array, etc.), client, or other computer system upon which e-commerce servers, websites, databases, web browsers and/or web analytic applications may be instantiated.

The optional illustrated exemplary server 22 with associated database 24, remote computing device 26 (which may also be referred to as an observer's computer), the optional patient virtual reality (VR) and/or augmented reality (AR) device 40 (which may also be described herein as a VR headset, VR/AR headset, VR/AR device, head-mounted display, smartphone, or the like), and the optional local computing device 38 (each of the preceding computers may also may optionally be described herein as a "client computer" in at least one embodiment in the case where the server 22 is part of the system, rather than the executable files, dictionaries, and databases, etc. being locally installed, for example, on the smartphone inserted within the VR headset 40) are generally known to a person of ordinary skill in the art, and each may include a processor, a bus for communicating information, a main memory coupled to the bus for storing information and instructions to be executed by the processor and for storing temporary variables or other intermediate information during the execution of instructions by processor, a static storage device or other non-transitory computer readable medium for storing static information and instructions for the processor, and a storage device, such as a hard disk, may also be provided and coupled to the bus for storing information and instructions. The server 22 and client computers 30, 38, 40 may optionally be coupled to a display for displaying information. However, in the case of server 22, such a display may not be present and all administration of the server may be via remote clients. Further, the server 22 and client computers 30, 38, 40 may optionally include connection to an input device for communicating information and command selections to the processor, such as a keyboard, mouse, touchpad, microphone, and the like. Moreover, the client computers 30, 38, 40 may optionally include connection to an output device for communicating information and command selections to the patient or the therapist (or other observer), such as a speaker, etc.

At the outset, it should be noted that communication between each of the server 22 and client computers 30, 38, 40, and the database server 24 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes. It should also be noted that the terms "patient device" and "therapist device" (and equivalent names for computing devices that describe the user) are intended to include any type of computing or electronic device now known or later developed, such as desktop computers, mobile phones, smartphones, laptop computers, tablet computers, virtual reality systems, personal data assistants, gaming devices, POS systems, vending machines, unattended terminals, access control devices, point of interaction ("POI") systems, etc.

The server 22 and client 30, 38, 40 computers may also include a communication interface coupled to the bus, for providing two-way, wired and/or wireless data communication to and from the server and/or client computers. For example, the communications interface may send and receive signals via a local area network, public network, intranet, private network (e.g., a VPN), or other network, including the Internet.

In the present illustrated example, the hard drive of the server 22 (including an optional third party server and/or mobile app backend service, and the like) and/or one or all of the client computers 30, 38, 40 is encoded with executable instructions, that when executed by a processor cause the processor to perform acts as described in the methods of figures. The server 22 communicates through the Internet, intranet, or other network with the client computers 30, 38, 40 to cause information and/or graphics to be displayed on the screen, such as HTML code, text, images, and the like, sound to be emitted from the speakers, etc. The server 22 may host the URL site with information, which may be accessed by the client computers 30, 38, 40. Information transmitted to the client computer may be stored and manipulated according to the methods described below, using the software encoded on the client device. Although the computing devices are illustrated schematically as laptops and a virtual reality headset (with, for example, a smart phone held therein), the computing devices may include desktops, tablets, cellular devices (e.g., smart phones, such as iOS devices, ANDROID devices, WINDOWS devices, and the like), or any other computing device now known or later developed.

Still looking at FIG. 1, the computing devices may be one of many available computing devices capable of running executable programs and/or a browser instance. For example, they may be a mobile device, such as a tablet computer or a mobile phone device with computer capabilities, a laptop, a desktop, or other computing device. Executable instructions for the present method may be installed on the server 22 that hosts a web application caused to display a user interface on one or all of the client devices 30, 38, 40. Alternatively, executable instructions for all or at least part of the present method may be installed locally on one or more of the client devices 30, 38, 40, such as the smartphone within the VR headset 40. In a first example embodiment, the client devices 26, 30, 32 access and interact with the graphical user interface through a web browser instance, such as FIREFOX, CHROME, SAFARI, INTERNET EXPLORER, and the like, or through a desktop application. The web application is hosted on an application server with application hosting capabilities. In a second example embodiment, one or more of the client devices 30, 38, 40 access and interact with the graphical user interface through either a web application running on a mobile web browser or a mobile application (commonly called an "app").

Alternatively, executable instructions for carrying out all or at least part of the present method may be installed locally on one or more of the client devices 30, 38, 40. For example, one or more of the client devices 30, 38, 40 may be required to locally install an application on a smartphone device for carrying out all or part of the present method. In an example embodiment, an executable application file is installed on each of the devices 30, 38, 40 so that messages can be sent to and received from the server 22 (or between the devices 30, 38, 40), with the server sending, receiving, and/or relaying the messages to one or more of the client devices 30, 38, 40. The messages may be comprised of various forms of data, such as alpha-numeric text, pictures, animations, links, and so on. In yet another example embodiment, one party may have an application installed on the computing device, while the other party sends and receives messages through a browser instance.

In the most simple embodiment of the present system 20, all processes (sensing, calculations, data storage and manipulation, etc.) can be carried out on the patient computing device 40, which is preferably a VR/AR-ready, such as a modern smartphone or tablet held by hand or inserted into the headset, or a VR/AR headset or equivalent device with computing capabilities integral to the headset. In this case, the data can be accessed after the session by the observer O or other person (where an observer can be any number of people who not only observe, but may also participate in the discussion or therapy, such as a therapist (speech, occupational, etc.), a teacher, a psychologist, parent, and the like). The session data collected may be in raw form (with no analysis) and/or in an analyzed form to be reviewed on the patient computing device 40 or on a remote computing device 26 (such as a computer connected through the internet or intranet, etc.) or a local 34 computing device (connected wirelessly or by wire, etc.).

Still referring to the system 20 of FIG. 1, the patient P (generally an elementary age child) is shown wearing a VR headset 40. The headset can be a standalone headset— basically a wearable computer—or a smartphone or mobile VR headset—where a smartphone or the like is inserted into a slot within the headset and provides the computing power and display. Just a few examples of commercially available headsets include OCULUS RIFT, GOOGLE CARDBOARD, MERGE AR/VR, and so on. Although the patient P is shown wearing a VR headset 40, the patient P may also simply manually hold, for example, a smartphone or tablet, eliminating the VR headset 40. In fact, in at least some embodiments, all aspects of the present system and method may be carried out using just a single computing device held by the patient P interacting with the target object 44, a marker cube in this illustrated embodiment, which is discussed in greater detail below. Further, the patient P may simply manipulate the target object 44 in view of a laptop or desktop camera, or a standalone camera connected to the laptop or desktop, while viewing the augmented reality images displayed on the laptop or desktop screen. The dashed lines diverging from the remote computer 26 camera 30 represent the camera 30 recording images or a live video feed which can optionally be displayed within a window on the local computer 38 or displayed on the VR headset 40 screen, perhaps to one side and within a small window. Because, in this example embodiment, the VR headset 40 camera 42 places the augmented reality images on and extending from the target object 44, the patient P can still observe the display 36 of the local computer 34 (as captured and displayed in real-time in the VR headset display) to view the video feed of the observer O or other information displayed. The camera 38 on the local device 34 can provide a third person view of the patient P during the session. In this manner, two video feeds may be transmitted to the remote computer 26 and displayed as two video feed windows on the display 28, where each ay be selectively resized or hidden, so that the observer O can view both the AR video feed and the real life third person viewpoint video feed simultaneously. In this way, the observer O can witness the patient P body language and exposed facial expressions to further enhance therapy.

The observer O may be a child psychologist, marriage/family therapist, behavior specialist, speech/language pathologist, occupational therapist, parent, teacher, screener (e.g., identifying students in need of intervention), and other mental health support providers. This is a person that may simply observe and communicate with the patient P directly, through a remote computing device 26, or may connect directly to a video output of the VR headset, or the smartphone/tablet, or other computing device (wired or wirelessly) to view the augmented reality images that the patient is also viewing. This third party viewing of the augmented video feed may be simply carried out by connecting a video cable from the patient's device to a monitor nearby. In yet another example embodiment, the observer O may view the raw data or data processed automatically within an automatic data processing module, where the processed data outputted may be data graphs, charts, etc., colors, audible data, or other processed data that aids the observer O in understanding and/or engaging the patient P.

In the illustrated example system 20, the server 22 may transmit and receive data to and from one or more of the observer's computer 30, the local computer 38, the VR headset 40 (or the smartphone therein). The server database 24 may store various dictionaries, libraries, databases, etc. so that data recorded and processed during therapy sessions can be received and stored and/or processed, processed data can be transmitted to the observer's computer 30 and/or the remote computer 38, various fiducial marker candidates can be compared to the marker dictionary, and various augmented reality images and/or animations can be associated with a particular marker can be transmitted to at least the VR headset to be overlaid atop the target object 44, as will be discussed in greater detail below.

As the patient P manipulates or simply observes the target object 44, the observer O, if remote, views the patient P activity displayed on the display 28, and can choose to speak to the patient P by speaking within audio range of the microphone 33, where the audio data is transmitted to one or both of the local computer 38 and the VR headset 40, which would be emitted through the speaker 39 and/or a speaker connected to the VR headset 40 or the smartphone therein. The patient P can also choose to speak into microphone 39 or the microphone connected to the VR headset 40 or the smartphone therein. In this way, the patient P and the observer O can discuss in real-time what the patient is perceiving or other guidance or observations.

Figure 3:
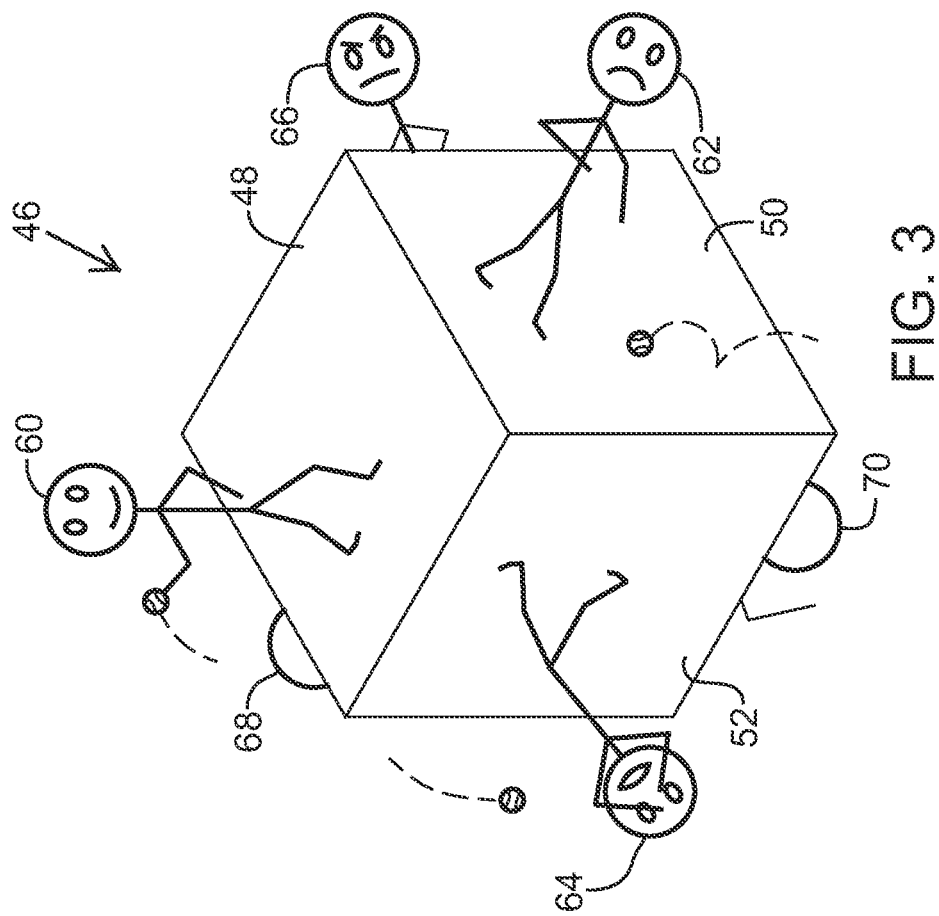
FIG. 3 is a simplified schematic perspective view of the exemplary object of FIG. 2 with a virtual image model overlaid on each face as viewed through the display of the computing device, in accordance with at least one embodiment.
Figure 2:
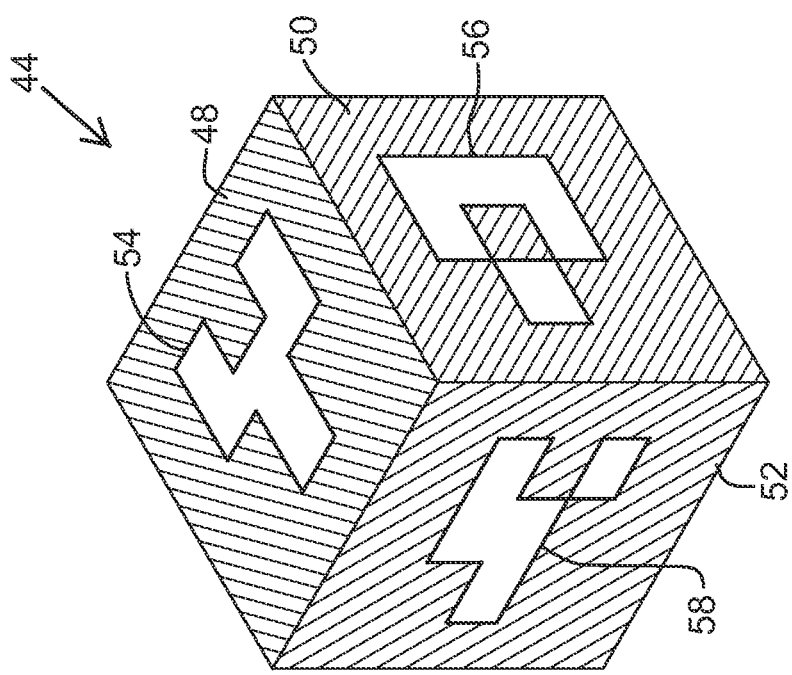
FIG. 2 is a simplified schematic perspective view of an exemplary object with at least one fiduciary marker detectable by the computing device, in accordance with at least one embodiment.

Referring now to FIGS. 1-3, the design of the target object 44 and its virtual augmentation with an 2D image, 2D animation, 3D image, or 3D animation is illustrated. In the illustrated embodiment of FIG. 2, the target object 44 is a cube of known dimensions with a unique fiducial marker on each of the six faces of the cube (that is, unique in comparison to one another) to facilitate the appearance of virtual objects, games, images, and animations overlaid atop the target object 44. Beyond establishing a unique identity, the fiducial markers serve as real world anchors of location, orientation and scale.

Although the target object 44 is disclosed as a cube, the target object can be any real object with at least one computer identifiable surface/face onto which an image can be positioned atop when viewed through a display in an augmented image or augmented video stream (e.g., a series of still images), preferably in real time. For example, the target object can be any multi-faced or single-faced object, such as a flat disk, rectangle, or plate of any outline, any polyhedron object, objects with planar or nonplanar surfaces (e.g., convex, concave, or other curved surface or complex surface). The target object 44 in at least one embodiment can have at least one unique computer-readable unique identifier (e.g., a fiducial marker) or can be markerless. In at least one example embodiment, the target object 44 can have multiple distinct unique computer-readable unique identifiers on a single face (e.g., organized in a rectangular grid pattern, array, or randomly, etc.), such that two or more distinct augmented images/videos can be overplayed relative to the identifiers. For example, in the single-faced object example embodiment, a 2×2 rectangular grid, a 2×3 rectangular grid, a 3×3 rectangular grid, etc. can be arranged on a sheet.

In the illustrated embodiment of the target object 44, the first face 48 includes a first fiducial marker 54, the second face 50 includes a second fiducial marker 56, and the third face 50 includes a third fiducial marker 58 (such as an ARTag, or the like). Because this illustrated target object 44 is a cube with six sides, three additional sides each with a unique fiducial marker are hidden from view in FIG. 2. The fiducial markers 54, 56, 58 can be painted with a reflective material against the black or non-reflective background of the faces 48, 50, 52, although other contrasting or non-contrasting arrangements are available. A contrasting and/or reflective coating, paint, material, etc. outlining or filling the area of the fiducial markers 54, 56, 58 creates unique identifiers that are easily detectable by the present system 20 or computers within system 20 by analysis of the markers detected in a real world image or video stream containing the target object 44. Although, the fiducial markers 54, 56, 58 are illustrated as square binary fiducials, the markers can be one or all of image or square image fiducials, square fiducials, and calibration fiducials. The calibration fiducials are used to calibrate the computer camera and provide accurate pose estimates in the perspective transformation process, as discussed further below. A number of planar fiducial systems are known, such as QR codes, data matrix, ARToolkit, ARTag, ARKit 2, and the proprietary fiducial system created by MERGE LABS, INC. for use on their MERGE CUBE.

The software application of the present system 20 and method is optionally preprogrammed with known qualities of the target object 44 and the fiducial markers 54, 56, 58 mounted thereon. The shape, dimensions, and other qualities of the target object 44 are accessible via communication with a local database and/or remote database or other form of data storage, either being preprogrammed or being variable where the qualities are entered manually through a user interface or automatically by accessing libraries or dictionaries of target object properties and fiducial marker properties.

In at least one example, the specific properties of the MERGE CUBE is optionally preprogrammed in the software application of the present system and method, where the cube shape is defined as having six faces with a specific fiducial marker on each face or at least an identifiable portion of the fiducial marker on each face (to account for a simplified fiducial marker where some of the markings are deleted or to account for partial obstruction or obfuscation of the fiducial marker, e.g., the fiducial marker is partially obscured by the users hand). In the MERGE CUBE example, the 72 mm dimension for each edge of each face is preprogrammed or can be accessed, the footprint of the fiducial marker or similar dimensional data (e.g., the width of the non-reflective space about the peripheral edge of each face, where the marker is set back from the edges) can be optionally preprogrammed or can be accessed, and the exact pattern of each of the six fiducial marker can be optionally preprogrammed or can be accessed, the order of placement of the fiducial markers on the cube can be optionally preprogrammed or can be accessed (which markers are adjacent to the surrounding markers), and the orientation of each fiducial marker relative to the others can be optionally preprogrammed or can be accessed. The specific design, the dimensions, and relative face positions and of the target object 44 and each of the fiducial markers 54, 56, 58 mounted thereon is known by the system, making it possible to quickly identify which side(s) of the target object 44 is facing the camera, and predict the adjacent faces not in view of the camera. At least some or all of these physical qualities of the target object 44 can be stored in memory in a library, such as one or more of a vision processing library, a fiducial marker dictionary, and/or similar databases, and retrieved by one or more the computers in the present system 20. Thus, as illustrated in FIG. 1, the system 20 can quickly place an image corresponding to the face of the target object 44 in view of the camera 42 atop without the needing to detect more than one or two faces.

FIG. 3 illustrates a schematic still image of the augmented reality video stream produced by the present system 20, as viewed by the patient P, with virtual imagery overlaid on the target object 44 in an augmented target object image 46. More specifically, in this example embodiment, a 3-dimensional animation model is positioned over a corresponding fiducial marker, for at least each side exposed to the camera 42. As described above, the present method in one at least one embodiment is preprogrammed with the physical qualities of the target object 44, with each of the six faces of the target object 44, a cube in this example, is uniquely identified. Thus, the present system 20 can predict the adjacent faces of the target object 44 even when out of view. For example, in FIG. 3, the fourth image model 66 and fifth image model 68 are partially in view on the augmented reality video stream although their corresponding or associated respective faces of the target object 44 are out of view. As the target object 44 is rotated towards one or both image models 66, 68, the image models will come into full view. Whether the image models 60, 62, 64, 66, 68 are in full or partial view, they are animated in at least one embodiment.

The image models 60, 62, 64, 66, 68 in the augmented target object image 46 illustrate several of the many possible scenarios which enable exploration of emotions, language, and social skills, through the system 20, by the patient P, with guidance from the observer O (a therapist or other professional, etc.).

Figure 4:
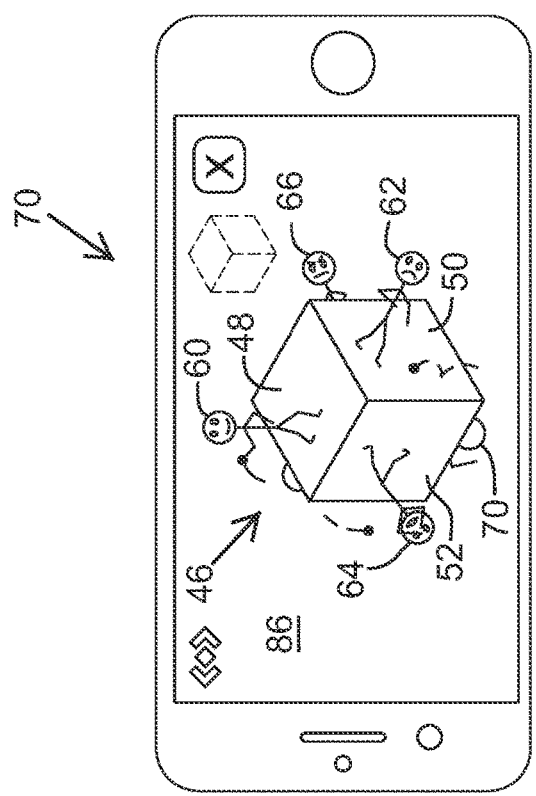
FIG. 4 is a simplified schematic plan view of an exemplary computing device, namely a VR/AR ready smartphone, tablet, or other compatible computing device, showing the main menu of the present application graphical user interface.
Figure 6:
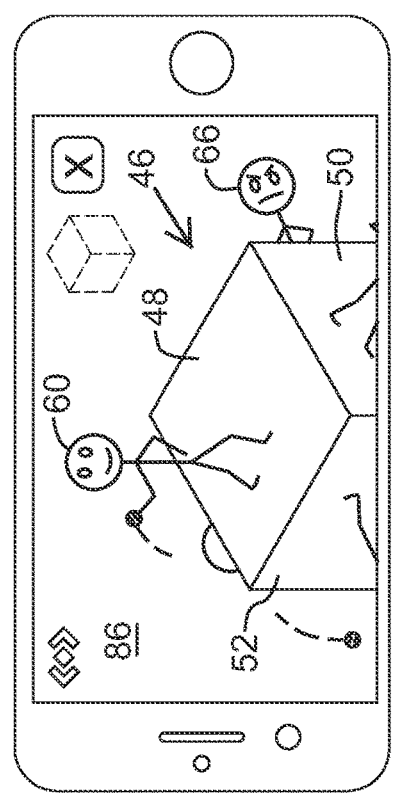
FIG. 6 is a simplified schematic plan view of the exemplary computing device of FIG. 4, showing the augmented reality graphical user interface displaying the target object with the augmented reality images laid overtop.
Figure 5:
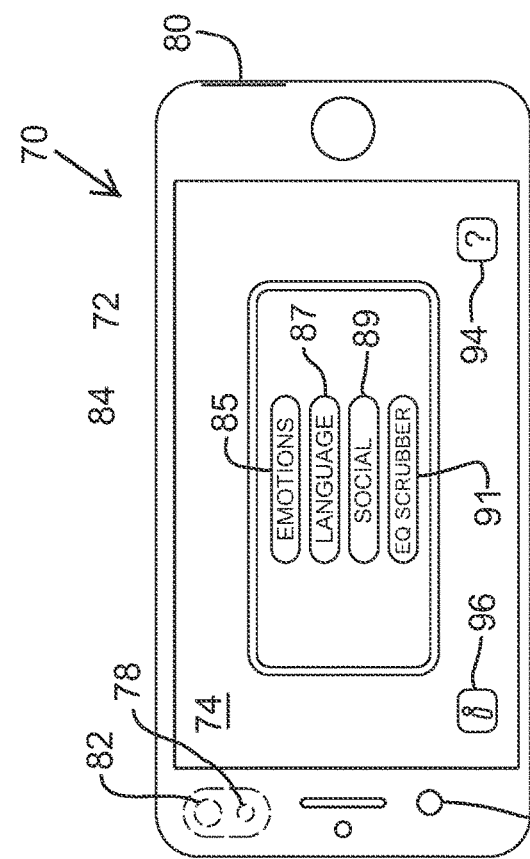
FIG. 5 is a simplified schematic plan view of the exemplary computing device of FIG. 4, showing the augmented reality graphical user interface displaying the target object with fiducial markers during the capture process, without the augmented reality images laid overtop.
Figure 7:
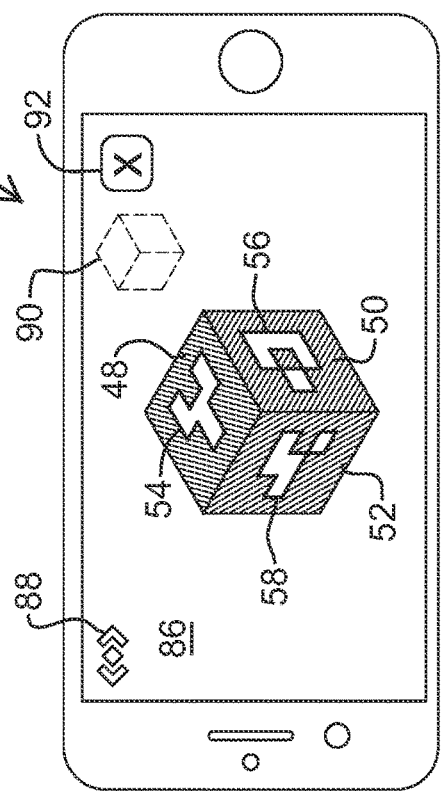
FIG. 7 is a simplified schematic plan view of the exemplary computing device of FIG. 4, showing the augmented reality graphical user interface displaying the target object with the augmented reality images laid overtop, in a first display example.

Referring now to FIGS. 4-6, an exemplary patient computing device 70 is illustrated, which is a smartphone 72 in this example 72, which may form a part of or the whole system 20. The exemplary smartphone 72 generally comprises a touch display 74, at least one camera (but will generally have a front facing camera 76 and a back facing camera 78 opposite the front facing camera 76), a light 82, and a speaker 80. FIG. 4 illustrates a exemplary main menu 84 for navigating the various modules and settings of the present system, displaying four menu option touch buttons, including the emotions module button 85, a language module button 87, a social module button 89, and an EQ scrubber module button 91. Other menu options may be provided to navigate the various features of the application, such as a frequently asked questions button 94, an information button 94, and so on.

In FIG. 5, one of the module buttons has been selected ("Emotions", for example) by the patient P (or any user) which causes the initial augmented reality screen 86 to display a video stream of the real world, including the target object 44 and any other objects in view (such as a hand holding the target object 44, background objects, etc.), where the video feed is received from the back facing camera 78 (or any connected camera, including the front facing camera 76). Included on the initial augmented reality screen 86 is a AR mode button 88 in which the augmented reality mode can be chosen, such as the virtual reality mode (using a VR headset to view a split screen) or the phone mode (viewing the screen of the smartphone directly and without a VR viewing device) and the light 82 may be activated or deactivated. Further provided as an option, is a virtual object mode button 90, where the user can choose to view the virtual images 60, 62, 64, 66, 68, 70 arranged together to form a video feed displaying what looks like the augmented target object image 46 of FIG. 6, without requiring a physical target object 44 in front of the camera 82. However, the patient P (or other user) must touch rotation buttons (not shown) to move the virtual object, rather than manually manipulating the real life target object 44 in augmented reality mode. Activating the close screen or exit button 92, causes the application to display the main menu 84.

Looking still at FIGS. 5-6, and in FIG. 5 in particular, the target object 44 is displayed in the real world environment, held by hand, set on a platform, a table or other surface, or rolled on a surface like a die for a random effect. The screen 84 will momentarily display the target object 44 without the augmented overlay, with the fiducial markers displayed, during the capture process. In the capture step, the video stream or digital image is received by the image processing application from the camera 78, where the incoming video stream is scanned for 2D fiducial marker candidates, which could include any fiducial marker on the target object 44, if in camera view, and may include any other candidate objects in the background that are somewhat similar to a fiducial marker. In at least some embodiments, a perspective transformation can be applied to the fiducial marker candidates to obtain a marker is canonical form. In other words, if the fiducial marker candidate appears to be equilateral in shape when viewed at an angle, when the preprogrammed fiducial markers are known to be square and of a specific dimension, then it canonical form would a square. The image processing application then analyzes the bits of the inner codification to determine if the fiducial marker candidate matches a preprogrammed/predetermined fiducial marker within the fiducial marker dictionary/library, where non-matching candidates are rejected. In this way, in at least one embodiment, the valid fiducial markers can be quickly analyzed by image processing application, and the remaining hidden fiducial markers (hidden on the side or back end of the cube) can be predicted with high accuracy due to the known qualities of the target object 44.

Furthermore, in preparation for rendering an image overtop each fiducial marker and for target object 44 tracking purposes, the position and rotation of the target object 44 and the smartphone (or other VR/AR enabled computer) is calculated from measurements collected from various sensors and/or images, for example, using positional data collected by the smartphone sensors with known portions of the fiducial marker that act as a calibration fiducial to estimate the position and rotation of the target object 44, in one or more embodiments. Positional sensors are integral to VR/AR ready smartphones and computers, such as an accelerometer, a magnetometer (compass), and a gyroscope, which can be used to determine the camera pose (position and rotation) in the real world and relative to the environment, and/or at least one fiducial marker on the target object 44 and/or the target object 44 itself. The data collected from inertial sensors, such as one or more of the accelerometer, the magnetometer, and the gyroscope are manipulated in the present algorithm to calculate the position (x, y, z) (or translation over time) and rotation ($\psi$, $\theta$, $\phi$) (yaw, pitch, and roll) of the smartphone, to measure the smartphone's movement in three-dimensional space with six degrees of freedom, and relative to the target object 44, using, for example, the VUFORIA ENGINE.

The calculated values, (x, y, z) and ($\psi$, $\theta$, $\phi$), (and in at least one embodiment, the image scale) are then applied to the target object 44 to measure its rotation and position relative to real world and/or the camera of the smartphone, by automatically tracking at least one point on the cube, generally all or a portion of one or more fiducial markers, such that the position of at least one fiducial marker can be determined throughout a session, with the position of the remaining fiducial markers being known relative to the tracked fiducial marker. This data is used by the algorithm to automatically calculate the movement of the target object 44, or part thereof, through a three-dimensional virtual coordinate system.

After one or more fiducial markers have been identified on the target object 44, a 2D or 3D model is rendered atop or nearby the visible fiducial markers and atop of or offset from all fiducial markers when the rendered animation model is at least partially visible, where the model is rendered and aligned in the scene in an accurate and visually acceptable way (e.g., sideways, upside down, at an angle, etc., as well as being scaled (larger or smaller) to fit the face of the target object 44, as viewed on the screen 72. Referring to FIGS. 3 & 6, in at least one exemplary embodiment, the first image model file 60 is associated with the first fiducial marker 54 on the first face 48 of the target object 44. Likewise, the second image model file 62 is associated with the second fiducial marker 56 on the second face 50 of the target object 44. And, the remaining four image model files are similarly associated with a respective fiducial marker on separate faces, where the associations between fiducial markers and image model files depends on the mode of the application, described in greater detail below. As the target object 44 is rotated and translated in real space the image model files are likewise rotated and translated, and scaled up or down.

There are numerous file formats for the image model files compatible with the present application and system 20. For example, the GL transmission format (gITF) for three-dimensional models may be imported into the application and animated through use of code, for example, HTML and JavaScript. Animated virtual objects are generally preferred in at least one embodiment of the present system, since complex social scenes can be played out much more effectively through animation. In at least one embodiment, the animation is looped and repeats every 1-3 seconds, to quickly convey a focused scenario designed to evoke an emotional response or other reaction from the patient P. Of course, a two-dimensional image or animation can be rendered overtop the fiducial marker using a known file format, such as a graphics interchange format (GIF) file or the like.

In at least one exemplary embodiment, the coordinate data is collected and recorded, to be stored (i.e., on the smartphone memory running the present augmented reality application) and/or transmitted to a remote database 24 on server 22 and/or transmitted to a observer's computer 26 and/or a local computer 34 (not the smartphone). In one example, the coordinate data can be transmitted from the smartphone 70 (either inserted within the VR/AR headset 40 or held by hand) to another computer, smartphone, server, etc., either physically wired to the smartphone 70 or headset 40 or in wireless communication with the smartphone 70 or headset 40, either in real time as data is collected or at some other point. Any one of or all of the coordinate data, time data, accelerometer data, compass data, gyroscope data, and other pertinent or otherwise useful data can be collected and stored and associated with a particular patient P. The data may be recorded every second or fractions thereof. For example, data acquisition one or both of the real world data and virtual world data may be recorded at a sample rate of between 1-100 Hz. The time of the session is also recorded in one or both seconds and or clock time (e.g., $t_i=0$ and $t_f=T_S$ or $t_f-t_i=T_S$ where $T_S$ is the total time of the session in seconds). Further, portions of the session, automatically partitioned by the algorithm of the present application, are recorded and transmitted in at least one embodiment, as described further below.

The data acquired in each therapy session is manipulated by the present system 20 through use of an algorithm which determines on which face of the target object 44 the patient was most likely focused for any given point in time, through use of one or more measured factors, such as time, position, orientation, scale of image, area of faces, and other factors which can be indicative of patient P focus on a particular face or faces. As discussed above, the physical qualities of the target object 44 are known and are preferably programmed as part of the present application, or can be looked up by the present application, or entered by a user, or detected automatically through a calibration process. With the present exemplary cube design of the target object, the dimensions of each face is known (e.g., 72 mm) and/or the dimension of the fiduciary marker is known (or the marker contains scaling or dimensional data readable by a computer). With this data (and other collected data, if needed) the algorithm can determine which face and its associated image/animation model has the highest likelihood of being the patient's center of visual focus and/or attention within a particular period of time.

In at least one embodiment, the present algorithm can determine which face of the target object 44 is facing completely or at least partially upright (or any other direction, such as downwards or laterally, with gravity pulling in the downwards direction) in the real world and/or as displayed in the screen, where the accelerometer can provide a gravitational vector parallel to the z-axis. In the illustrated example embodiment of FIG. 6, the first face 48 is positioned substantially upright (for example, within 5° tilt of being upright, within 10° tilt of being upright, within 15° tilt of being upright, within 20° tilt of being upright, or within 30° tilt of being upright), where the smartphone's positional data is used to determine that the smartphone is being held in landscape orientation (where the longer sides of the screen 84 are being held more parallel to the ground than the shorter sides) or in portrait orientation (where the shorter sides of the screen 84 are being held more parallel to the ground than the longer sides) or an angle in between.

Further, still as shown in the screen image of FIG. 6, just the calculated, estimated, or measured coordinates of the target object 44 can be used to determine the face on which focus is trained. For example, still assuming in at least one embodiment that the face that is upright is the face on which the patient's focus is trained, coordinate data (e.g., the position (x, y, z) and rotation ($\psi$, $\theta$, $\phi$), and/or multiple position coordinates, and/or coordinates calculated by a computer vision technology system or other system using one or more of the position, rotation, and image data), established at the start of the session or reestablished at some point in the session, are manipulated by the algorithm to determine the orientation of at least one face of the target object 44 or orientation of some other portion at each point in time; and therefor, determine which face is upright (first face 48 in this illustration) or nearly upright or most upright compared to the remaining faces.

In at least one embodiment, each face (and/or or region/area of the face or a point on the face) of the target object 44 is assigned as being between a range of a first coordinate or set of coordinates and a second coordinate or set of coordinates, so that the application running the algorithm can determine a region of focus (e.g. the face of the target object 44 upon which the patient's attention is estimated to be focused and/or trained upon based upon the estimated orientation and position of the target object 44), with each face including a fiducial marker (or the faces may be markerless, in one or more embodiments). As mentioned above, there are multiple methods of tracking the position and orientation of the target object 44 as it moves through the real world in front of the camera 42, including coordinate systems enabling tracking of the target object 44 in three-dimensions and with six degree of freedom, and thereby enabling the calculation of coordinate data periodically (such as 1 time per second or 10 times per second).

In one or more example embodiments, the target object 44 is a cube 45, as illustrated in FIG. 5 and other figures, and the cube includes a first face 48, a second face 50, a third face 52, and not in view in the illustrated cube 45 but readily apparent, a fourth face, a fifth face, and a sixth face. In the present cube-shaped target object 44 example, each of the six faces and their respective fiducial markers on each face, is assigned a range of coordinates. The range of coordinates for each face be statically assigned and/or can change from session to session where the range or coordinates assigned can be randomly assigned or assigned according to which face is detected at the start of the session.

In this exemplary embodiment, the first face 48, is assigned a first range of coordinates (e.g., for position and rotation), comprising a first lower range limit of ($x_{1min}$, $y_{1min}$, $z_{1min}$) and ($\psi_{1min}$, $\theta_{1min}$, $\phi_{1min}$) for and a first upper range limit of $(x_{1max}, y_{1max}, z_{1max})$ and $(\psi_{1max}, \theta_{1max}, \phi_{1max})$, where $x_{1min}, y_{1min}, z_{1min}$ are positions in a space (virtual and/or real-world) having standard units (e.g., mm, pixels, etc.) or units created by the application, and where $\psi_{1max}, \theta_{1max}, \phi_{1max}$ are rotational orientations in space having standard units (e.g., degrees, radians, etc.) or units created by the application. Likewise, the second face 50, is assigned a second range of coordinates comprising a second lower range limit of $(x_{2min}, y_{2min}, \text{and } z_{2min})$ and $(\psi_{2min}, \theta_{2min}, \phi_{2min})$ for and a second upper range limit of $(x_{2max}, y_{2max}, z_{2max})$ and $(\psi_{2max}, \theta_{2max}, \phi_{2max})$. Further, the third face 52, is assigned a third range of coordinates comprising a third lower range limit of $(x_{3min}, y_{3min}, z_{3min})$ and $(\psi_{3min}, \theta_{3min}, \phi_{3min})$ for and a third upper range limit of $(x_{3max}, y_{3max}, z_{3max})$ and $(\psi_{3max}, \theta_{3max}, \phi_{3max})$. And, in a like manner, each of the fourth face, the fifth face, and the sixth face are assigned respective ranges of coordinate (e.g., a fourth range of coordinates, a fifth range of coordinates, and a sixth range of coordinates). Preferably, in at least one embodiment, part or all of the active face (the face upon which the patient's focus is estimated to be trained upon, which can shift between faces according to the movement of the target object 44 and/or the camera 78) can be found positioned within at least one of the ranges of c Still referring the example embodiment of FIG. 6, the target object 44 is tracked over time, with one coordinate data set being automatically calculated each second (for example) as the target object 44 is moved by the patient P. Table 1 below illustrates the data generated in a session in at least one method of tracking the target object 44.

TABLE 1

Session Data

| Time (s) | Position Coordinates | Rotation Coordinates | Active Face |
|---|---|---|---|
| 0 | $(x_0, y_0, z_0)$ | $(\psi_0, \theta_0, \phi_0)$ | Second Face |
| 1 | $(x_1, y_1, z_1)$ | $(\psi_1, \theta_1, \phi_1)$ | Second Face |
| 2 | $(x_2, y_2, z_2)$ | $(\psi_2, \theta_2, \phi_2)$ | First Face |
| 3 | $(x_3, y_3, z_3)$ | $(\psi_3, \theta_3, \phi_3)$ | First Face |
| 4 | $(x_4, y_4, z_4)$ | $(\psi_4, \theta_4, \phi_4)$ | First Face |
| 5 | $(x_5, y_5, z_5)$ | $(\psi_5, \theta_5, \phi_5)$ | First Face |
| 6 | $(x_6, y_6, z_6)$ | $(\psi_6, \theta_6, \phi_6)$ | First Face |
| 7 | $(x_7, y_7, z_7)$ | $(\psi_7, \theta_7, \phi_7)$ | Third Face |

Still looking at Table 1 above, the position coordinates and the rotation coordinates, in at least one embodiment, are used in the algorithm to calculate the face which is the active face at any given point of time or within a period of time ($\Delta t$). The coordinate data were collected as described above or similar operation, and are stored in a local or remote database, for example, in a delimiter-separated values (DSV) file, for further data analysis and transformation. The parameters for determining which face is active can include one or more of determining which face is in the upright position and/or substantially upright, determining which face occupies the greatest screen area (e.g., calculating the area of each displayed face in pixels to determine the largest are in pixels and the like), determining patient P eye is focused utilizing eye tracking technologies (e.g., measuring the point of gaze and/or the motion of the eye), detecting patient P interaction with the device screen or a particular face of the physical target cube 44, and so on. Although the active face data collected and displayed in the active face column in this example describes the faces of the target object 44 that are active at each point in time, the specific animated scenario displaying an emotion, social situation, action, etc. can be stored in place of the active face data or in addition to the active face data, as the same face (for example the first face 48) has a number of animated scenarios which are displayed atop the face's fiducial marker, depending on the mode of operation (module) and the layer within that module. Thus, further data sets can be collected and stored describing the module and/or layer in which the application is being operated. A further data set and parameter for determining which face is active is data associated with a physical contact (e.g., a finger touch) with the screen, which indicates that the patient P likely desires further exploration of a specific social scenario.

Again, looking at the theoretical data set of Table 1 (with Greek letters used in place of the numbers of the real data set), it can be seen that the patient P either repositioned the camera or rotated the target object 44 to focus on a particular image model rendered atop its respective face. In this example, the patient P initially started on the second face 50, then quickly moved to focus on the first face 48, dwelling on the first face 48 for approximately four seconds ($\Delta t=4s$), before turning to the third face 52. As this is an exemplary data set for discussion and demonstrative purposes, the patient is likely to spend much more than four seconds on a face when focused.

Figure 8:
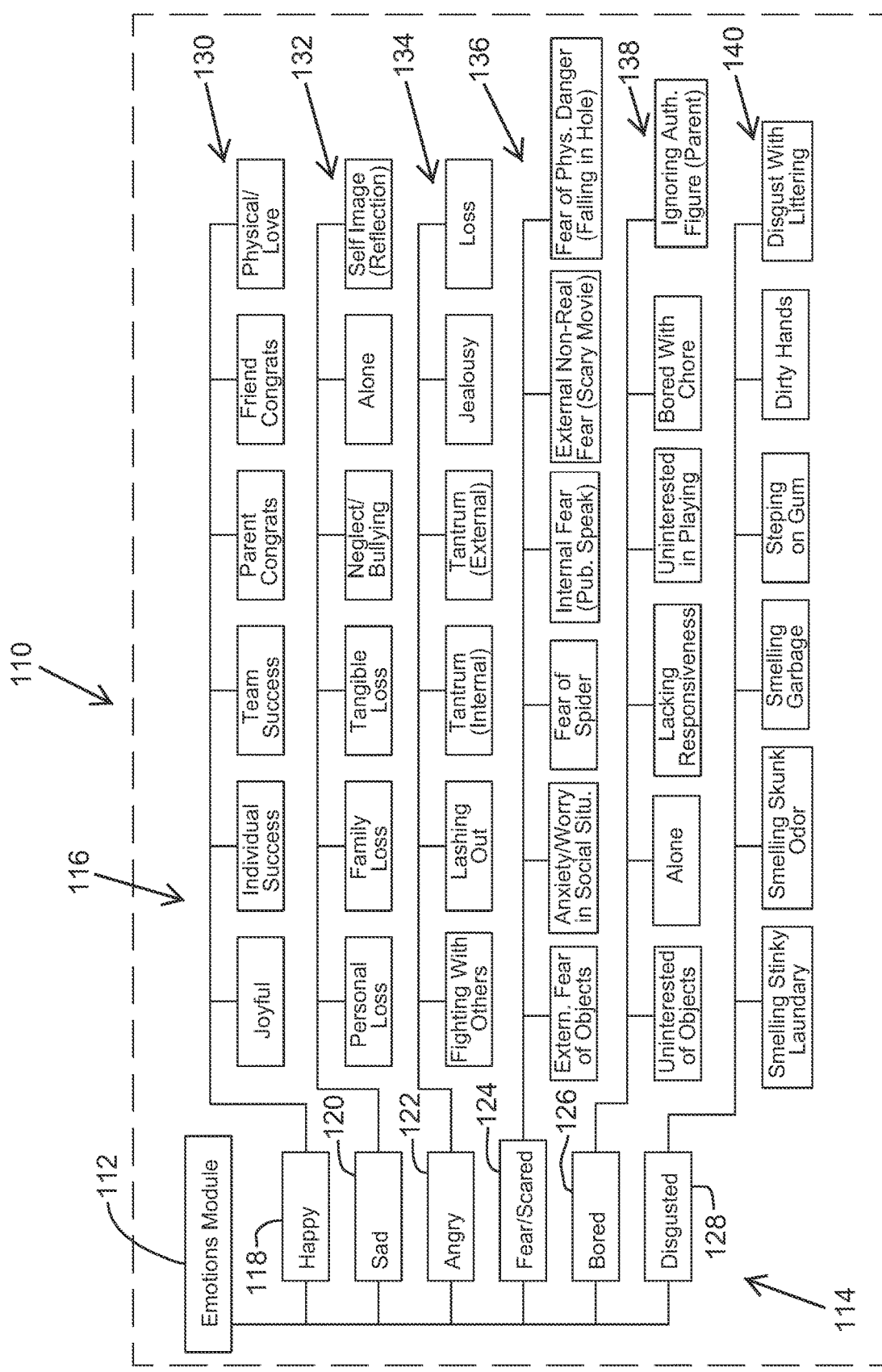
FIG. 8 is a simplified schematic view of an exemplary data analysis graphical user interface screen for viewing the therapy session and the data produced therein.

Looking now at FIG. 8, an exemplary observer graphical user interface 94 is schematically illustrated, and, in one or more embodiments, is displayed on the observer's computer 26, communicating to the observer real-time data collection, video feeds, and data analysis. In this example, various windows can be selectively activated to display information related to the therapy session. As described in the discussion regarding Table 1, a data feed 100 is displayed showing in real-time at least the active face, which in this case, described the an emotion, social situation, action, etc. estimated to be the focus of the patient's attention, based on, all or in part, the above-discussed parameters and/or factors. Further, the data feed 100 can include coordinate data, time data, and other forms of collected raw or manipulated data. The data feed 100 scrolls throughout the session and can be resized or reformatted to review a longer time period. The data feed 100 represents the data received in real-time during a therapy session and is further stored locally or remotely. In this example data feed 100, the target object 44 face associated with the emotion "sad" is the face upon which the most time is spent; and is thus presumed to be the active face for at least this time period. Further, the data feed 100 includes the patient P name or other identifier, as well as any data associated with that particular patient, such as data from prior sessions or personal or medical data. In the active face column, various therapeutic focus subjects are listed according to the module, layer, and active face at that moment.

The suggested talking prompt feed 102 can be displayed in one or more embodiments. The sets of questions, comments, directions, images, and other messages to the observer O (such as a therapist) are displayed, and are continually or periodically refreshed according to the active face or other detected patient P activity. In this example, it is automatically determined that face representing the "sad" emotion is the active face, and it is assumed by the application that talking prompts related to exploring sadness can be useful to guiding the observer O in his or her conversation with the patient P. For example, the first talking prompt displayed is "Are you thinking about anything bad that may happen?". The observer O may directly read the talking prompt to the patient P to encourage engagement and exploration of that emotional aspect; or the observer O may ignore one or more of the talking prompts or reword the taking prompts. This tool may be more useful for less experienced observers, such as parents, rather than the highly experienced therapist. The observer O, or other user and/or administrator, can write a set of talking prompts and associate each talking prompt with a particular emotion, social situation, action, etc., for training new employees, as a checklist, as a gentle reminder of the likely most appropriate discussion topics, or for other custom reasons. In the algorithm, the active face is determined, and the specific module and layer is determined, and the emotion, social situation, action, or other therapeutic subject associated with the active face while in that specific module and layer is automatically determined (for example, through a lookup table, library or other database storage means); and, thereafter, the therapeutic focus subject associated with the active face, module, and layer is displayed to the observer O, such as "angry", "sad", "scared", and so on.

Patterns may also be tracked throughout the current session or more than one session. For example, if the patient P continually returns focus on a particular emotion, even after viewing other faces, the algorithm can track the frequency and dwell time for that emotion to determine whether that subject area should be further explored, even though individual views of the face associated with the subject area are short (at least from the observer's viewpoint). In one example, the total dwell time spent on each individual face (including module and layer) is recorded and summed throughout the session and/or at the end of the session to so that viewing patterns not readily apparent to the observer O in real-time are calculated and displayed to the observer O. To reduce noise and/or false positives in the data, dwell time below a minimum time threshold can be eliminated from the calculations as to filter irrelevant data from the summation or other calculative process. For example, the minimum dwell time may be 2 or more seconds, 3 or more seconds, 4 or more seconds, 5 or more second, 10 or more second, 15 or more seconds, 20 or more seconds, and so on.

To aid the observer O in understanding the experience of the patient P, a patient video feed 96 can be displayed, where the patient video feed 96 shows the patient's P face and/or body and/or the target object 44, as recorded, for example, by camera 38 or a standalone camera. In this way, the observer O can visually witness the facial and body language of the patient P to further aid in understanding the patient's P experience. This is useful for remote therapy sessions, where the observer O is a distance away from the patient, such as another room or thousands of miles away. Further, it can be useful to record the sessions as streamed in the patient video feed 96 for patient records, for the purpose of second opinions, for parent or guardian viewing, for later patient P viewing, for record keeping, or for other therapeutic or non-therapeutic purpose. Moreover, camera 30 can stream an observer video stream 98, so that the observer O can view himself or herself during the session, so that the patient P can see the observer O where the observer video stream 98 is displayed on the local computer 34, where the observer video stream 98 can be observed through the AR headset 40 (as displayed on the local computer 34 display 36 or directly on the headset 40 screen) or viewed with the naked eye when using a smartphone 72 instead of the AR headset 40.

In one or more embodiments, the observer GUI 94 can include a window that displays a stream the video output of the patients AR headset 40 screen or the smartphone screen 72 in a patient screen mirror video feed 104. In this way, the observer O can view the exact scene being displayed to the patient P, to better understand the patient's experience. All of the above video streams 96, 98, 104 (and/or any audio conversations) can be stored in the patient P file or other memory, so that a complete record of the session can be maintained.

Still looking at FIG. 8, a data analysis GUI 106 is automatically produced by the present application, which graphically represents the analyzed data in an easy-to-understand format for quick communication of complex data to the observer O. In this example, the graph or visual image is a bar graph 108, which corresponds to the data collected. In this example bar graph 108, it can be seen that the bar representing the "sad" emotion is far taller than the other bars representing other emotions. Without looking at the data feed 100 window, the observer can quickly see that it is very likely that sadness should be further explored, although other factors, such as body language, may indicate otherwise. Of course, a number of other graphical representations of the data can be produced by the present algorithm, such as a pie graph, a scatter plot, one or more pictures and/or colors, and the like. The present example observer GUI 94 presents a powerful tool to guide the inexperienced observer O or to augment the judgment of the experienced professional observer O.

Figure 9:
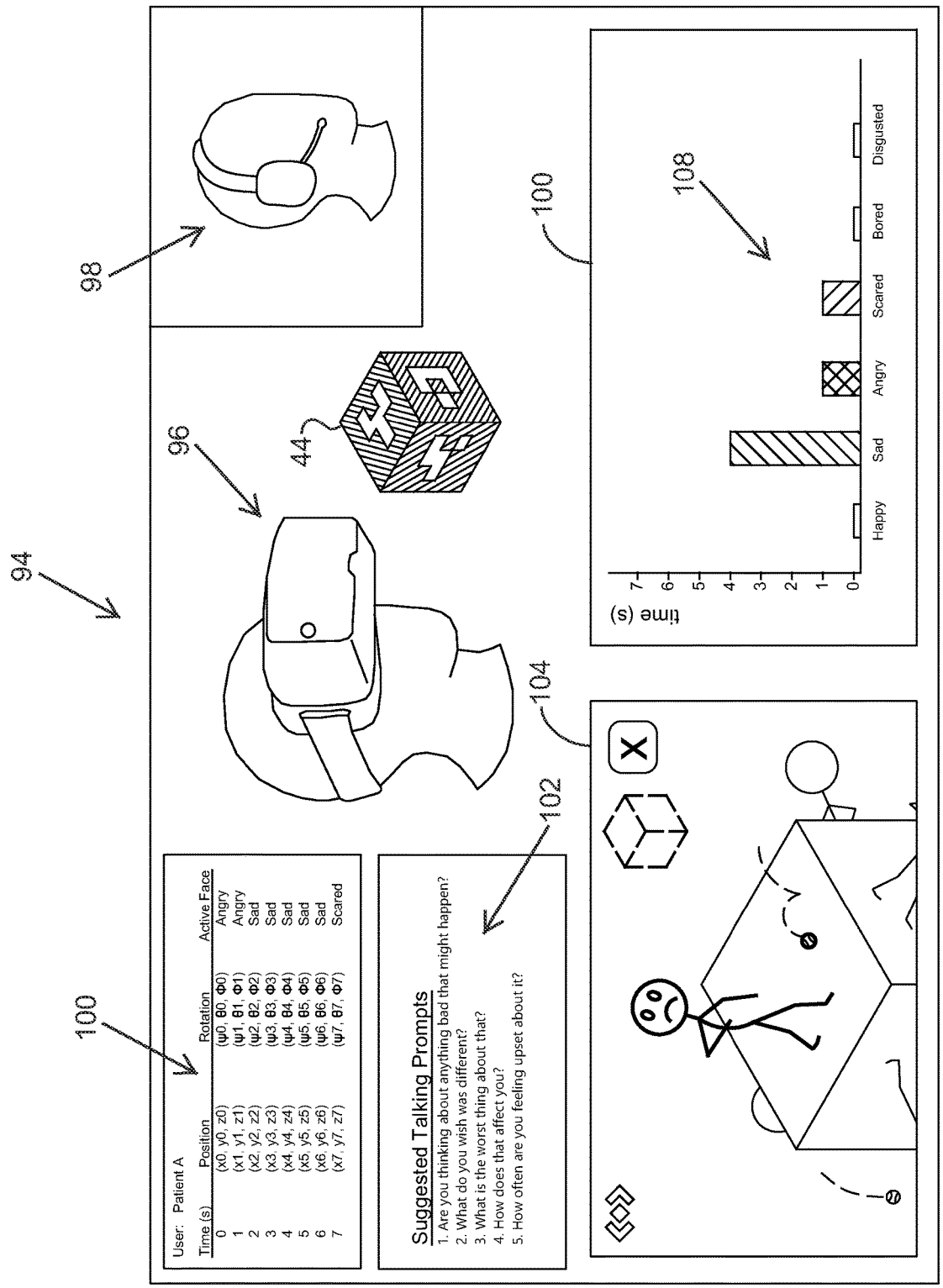
FIG. 9 a simplified schematic view of an example hierarchy diagram for the emotion module.

Turning to FIG. 9, as briefly discussed above, there are a number of modules and layers available to the patient P during a session. An example hierarchy diagram 110 is illustrated, showing the emotions module 112 and its various layers and sublayers. Because the exemplary target object 44 is a cube, there are preferably six layers 114 and six sublayers 116 (and further layers within each sublayer are possible). Of course, if a two sided object (such as a disk) were to be used, the hierarchy and layers would be configured differently, perhaps with only two layers. In use, the patient P (or other user) selects, for example, the emotions module button 85 (as shown in FIG. 4) which enables exploration of six layers 114 of emotions subjects, in one or more embodiments. For example, the six layers 114 in the emotions module 112 can include the happy layer 118, the sad layer 120, the angry layer 122, the fear/scared layer 124, the bored layer 126, and the disgusted layer 128. Each layer 118, 120, 122, 124, 126, 128 can be accessed through manipulation of the target object 44 and, in-part, the touchscreen 74 and/or wholly through the touchscreen 74 through the virtual object mode button 90. Thus, no physical target object 44 is required to access the various modules, layer, and sublayers; although a physical target object 44 is preferred in one or more embodiments, as the children often respond well to manual manipulation of a physical object.

When the emotions module 112 is active, six images or animations (a series of images) is displayed, each on a respective face of the target object 44. In an example embodiment, each emotion is represented by a three-dimensional animated character distinct in design and color from the remaining five animated characters. For example, when the emotions module 112 is selected from the main menu 84, the top level layer 114 for the emotions module 112 augments the target object 44 cube, such that animations representing the happy layer 118, the sad layer 120, the angry layer 122, the fear/scared layer 124, the bored layer 126, and the disgusted layer 128 are rendered atop their respective associated fiduciary markers. The patient P can rotate and translate the target object 44, which likewise, augmented target object image 46 displayed on the touchscreen 74, and touch touchscreen 74 atop the rendered image model which most interests the patient P at that moment. Colors may aid in the patient's P identification of the emotion, both in at the layers levels and sublevels, where each character and surrounding environment can be rendered mostly or at least in part a specific color, such as yellow for characters within the happy level and sublevels, blue for characters within the sad level and sublevels, red for characters within the angry level and sublevels, purple for characters within the fear/scared level and sublevels, gray for characters within the bored level and sublevels, and green for characters within the disgusted level and sublevels.

As an example (referring to both FIGS. 6 & 9), the first rendered image model 60 is associated with and rendered on the first face 48 atop the first fiducial marker 54. In this example, the first rendered image model 60 is associated with the happy layer 118 and displays an animated image representing happiness in general (such as a yellow-colored smiling character), so that touching the first rendered image model 60 on the touchscreen 74 calls up the six animated models associated with the happy sublayer 130, such that the augmented target object image 46 is augmented with six variations of scenarios related to happiness, such as being joyful, being happy over an individual success, being happy over a team success, being congratulated by parents, being congratulated by friends, and receiving physical love. Since there is just one sublayer in this example, touching the touchscreen 74 once again in the happy sublayer 130 will serve as a "go back" instruction, displaying the top level layer 114 once again. While the patient P is exploring the happy sublayer 130, the time spent on each face is recorded and/or transmitted as described above, such as the sad sublayer 132, the angry sublayer 134, the fear/scared sublayer 136, the bored sublayer 138, and the disgusted sublayer 140.

The present system 20, method, and devices can be used by a wide variety of people as a training tool for a wide variety therapeutic and social applications. The present system increases student engagement during individual or group counseling sessions, helping children identify feelings and emotions. The present system, method and devices includes several modules, such as the emotions module, the language module (abstract language), and the social skills module (social pragmatic skills), the very skills with which children with autism have the greatest struggles. Further, the present system, methods, and devices can be used in high schools, in mental health clinics, by law enforcement, by social workers, by marriage counselors, and so on, for people of all ages. The subject matter presented and/or the manner by which it is presented can be adjusted according to the age and/or maturity of the patient.

The emotions module helps patients (school-age children, mainly) identify and label emotions. This is achieved by helping to identify different feelings and emotions through unique characters that can be viewed and interacted with in augmented reality. The student can manipulate the target object and/or the AR device to explore the various emotions; or the student can simply roll the target object and role play the emotion or discuss a time when they felt that way. The primary or top layer of feelings and emotions include happy, sad, angry, fear/scared, bored, and disgusted. Clicking or tapping on each individual character then introduces six variations or subtopics of that specific feeling/emotion.

In one embodiment, the disclosed system can portray six different characters and each character represents one of six different emotions. Clicking or touching an image or character representing an emotion introduces six variations of that specific emotion. This can help children better identify with their own emotions and learn how to start communicating about them. In other embodiments, the disclosed system can portray fewer than six different characters, such as, e.g., 2, 3, 4 or 5 different characters, with each character representing a different emotion. In yet other embodiments, the disclosed system can portray more than six different characters, such as, e.g., 7, 8, 9 or 10 different characters, with each character representing a different emotion. In each of these embodiments, clicking or touching an image or character representing an emotion introduces variations of that specific emotion.

In one embodiment, the emotions and variations of the emotions include i) Happy: joyful, individual success, team success, congratulating with parent, congratulating with friend, and physical/love; ii) Sad: personal loss, family loss, tangible loss, neglect/bullying, alone, and self-reflection (self-image); iii) Angry: fighting with others, lashing out, tantrum (internal), tantrum (external), jealousy, and loss; iv) Fear/Scared: external fear of objects, anxiety/worry in social situations, fear of spider, fear of public speaking/singing (internal fear), fear of a scary show (external non-real fear), fear of being scolded (real conflict), and fear of failing in hole (physical danger); v) Bored: uninterested in school, alone, lacking responsiveness with others/objects, uninterested in school, uninterested in playing, bored with a chore, ignoring parent (authority figure), ignoring dog (affection); and vi) Disgusted: physically sick due to external stimuli or perception to such stimuli, smelling stinky laundry, smelling skunk odor, smelling garbage, stepping on gum, dirty hands, and disgust with littering.

The abstract language module helps to facilitate further language development by teaching multiple verbs/actions through the characters. The observer (parent, teacher, therapist, facilitator, etc.) can encourage the student to use the action seen in a sentence or act out the scene. The abstract language module, on the top layer, helps children understand and start using verbs. Children with autism are challenged learning action words due to their abstract nature. The abstract language module demonstrates each action through animation using interesting and engaging characters. In one embodiment, there are three layers in the abstract language module for each concept. Thus, in one embodiment, instead of using each of the six sides of the cube to display a unique image, a single image or animation is rendered atop the target object, where the student touches the screen to change between variations or subtopics. The each verb scenarios and variations/subtopics include i) Happy: kicking a soccer ball, running, and throwing; ii) Sad: eating, crying, and singing; iii) Angry: jumping jacks, weight lifting, and resting; iv) Fear/Scared: drinking, push-ups, and opening a door; v) Bored: raising hand, sweeping, and clapping hands; and vi) Disgusted: reading, sleeping, and swimming.

The social skills module helps lead discussion and role-play through social scenarios for social skill development. The students can roll the target object for a random social skill scenario. The students can take turns talking about the interaction occurring for example, "What do you think they are saying?" "Have you had a similar experience?". This module focuses on social pragmatic skills, which is an area with which children with autism struggle. In the layers of the module, there are various social scenes that the therapist is able to talk through with older kids with autism who are struggling with pragmatic skills.

In one embodiment, the social skills scenarios include i) helping person up from ground or person helping you up from ground; ii) playing blocks with friend; iii) talking/seeing something with friend; iv) high-five/congratulating friend; v) laughing at friend's/own discomfort; vi) comforting person or person comforting you; vii) sharing extra ice cream cone; and viii) playing ball with friend.

The EQ scrubber (emotional quotient) permits the child to scrub through the different levels of emotions per character from the lowest level 1 to the highest level 5 (or i through v) (e.g., sliding a finger across the touchscreen to move a GUI slider or the like). In one embodiment, the emotions and levels include i) Happy: smiling; joyful/dancing around; personal accomplishment/high marks on school assignment; congratulations from parent; and physical/love; ii) Sad: alone; crying; personal failure/failing school assignment; lost dog; and low self-image; iii) Angry: upset; stewing; angry yell; slamming door/tantrum; and breaking toy/tantrum; iv) Fear/Scared: scared looking around; scared shaking; scared of external object; fear of being scolded; and fear of physical danger/failing in hole; v) Bored: alone; alone with nothing to do (anxious); bored with playing; indifferent to authority figure (parent); and indifferent to affection (dog); and vi) Disgusted: disgusted generally; disgusted with dirty hands (perceived); disgusted stepping back; stepping on gum; and disgust with littering.

Aspects of the present specification may also be described as follows:

1. A method for objectively tracking and analyzing the social and emotional activity of a patient using a computing device, the method comprising the steps of: implementing an augmented reality tracking application in memory on the computing device; upon the augmented tracking application being initialized on the computing device, detecting by at least one camera a target object manipulated by the patient, the target object comprising a first face and a second face, a first fiducial marker positioned on the first face and a second fiducial marker positioned on the second face; detecting at least one of the first fiducial marker and the second fiducial marker; displaying on a screen of the computing device an augmented image overlaid on the target object, the augmented image comprising a first image associated with the first fiducial marker and a second image associated with the second fiducial marker; detecting a position and a rotation relative to the camera of the target object for each point in time for which a data point is collected; calculating a coordinate data set of the target object based on the position and the rotation detected; determining an active face for each point in time using the coordinate data set and a parameter indicative of the patient focusing attention on one of the first image and the second image, wherein the active face can be dynamically assigned to one of either the first face or the second face at each point in time; and storing as a data set the data point for each point in time, the data point comprising the coordinate data set, the active face, and a time.
2. The method according to embodiment 1, further comprising further comprising the step of associating the first image with a first therapeutic subject and the second image with a second therapeutic subject, the data point further comprising the first therapeutic subject and the second therapeutic subject.
3. The method according to embodiments 1-2 further comprising the steps of transmitting the data set to a second computing device; and displaying to a user at least a portion of the data set on a second screen of the second computing device.
4. The method according to embodiments 1-3 further comprising the steps of recording a video of the patient; transmitting the video to the second computing device; and displaying the video on the second screen of the second computing device.
5. The method according to embodiments 1-4 further comprising the steps of transmitting a mirror video of the screen of the first computing device to the second computing device; and displaying the mirror video on the second screen of the second computing device.
6. The method according to embodiments 1-5 further comprising the steps of retrieving from memory one or more talking prompts comprising a first talking prompt associated with the first therapeutic subject and a second talking prompt associated with the second therapeutic subject; and communicating the talking prompts through the second computing device to a user.
7. The method according to embodiments 1-6 further comprising the steps of establishing a videotelephony session between the patient and the user to permit the transmission in real-time and audio-video signal.
8. The method according to embodiments 1-7 further comprising the steps of processing the data set to automatically create a graphical representation of the data set; and displaying the graphical representation on the second screen of the second computing device.
9. The method according to embodiments 1-8 wherein the target object is a cube comprising the first face, the second face, a third face with a third fiducial marker positioned on the third face, a fourth face with a fourth fiducial marker positioned on the fourth face, a fifth face with a fifth fiducial marker positioned on the fifth face, and a sixth face with a sixth fiducial marker positioned on the sixth face.
10. The method according to embodiments 1-9 further comprising the steps of: displaying a second augmented image in place of displaying the first augmented image upon receiving an input activating a first image link, the second augmented image comprising a third image associated with the first fiducial marker and a fourth image associated with the second fiducial marker; and displaying a third augmented image in place of displaying the first augmented image upon receiving a second input activating a second image link, the third augmented image comprising a fifth image associated with the first fiducial marker and a sixth image associated with the second fiducial marker.
11. The method according to embodiments 1-10 further comprising the steps of: determining, for the second augmented image, the active face for each point in time using the coordinate data set and the parameter indicative of the patient focusing attention on one of the third image and the fourth image, wherein the active face can be dynamically assigned to one of either the first face or the second face at each point in time; and determining, for the third augmented image, the active face for each point in time using the coordinate data set and the parameter indicative of the patient focusing attention on one of the fifth image and the sixth image, wherein the active face can be dynamically assigned to one of either the first face or the second face at each point in time.
12. The method according to embodiments 1-11 further comprising the steps of: associating the first image with a first therapeutic subject and the second image with a second therapeutic subject, the data point further comprising the first therapeutic subject and the second therapeutic subject; associating the third image with a first subject first subtopic of the first therapeutic subject and the fourth image with a first subject second subtopic of the first therapeutic subject, the data point further comprising the first subject first subtopic and the first subject second subtopic; and associating the fifth image with a second subject first subtopic of the second therapeutic subject and the sixth image with a second subject second subtopic of the first therapeutic subject, the data point further comprising the second subject first subtopic and the second subject second subtopic.

13. The method according to embodiments 1-12 wherein the step of determining the active face for each point in time using the coordinate data set and the parameter indicative of the patient focusing attention on one of the first image and the second image, wherein the parameter is one or more of determining which of the first face and the second face are oriented more upright compared to the other, determining which of the first face and the second face has a larger screen area, and determining which of the first face and the second face has received a touch input.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the system, methods and uses disclosed herein.

Example 1 Clinical Study 1

The disclosed system was trialed with a group of 5th grade male students whose group focus had been on "Peer Pressure." In this study the primary mode of presentation was a three dimensional cube with unique fiducial marker on each of the six face. The target object was placed on the table and the student was allowed to hold a computing device which was running the computer implemented system, enabling the student to view all 6 characters (Happy, Sad, Angry, Disgust, Fear, and Bored) simultaneously. After defining each character, a facilitator then prompted the student with a question, such as, e.g., "Think about how you've been feeling lately, which one would you say looks the way you feel." The student would then be allowed to interact with the screen of the computing device to select the character most accurately representing the student's emotion. After selection of an emotion, a student could then rate the degree of that emotion using the Likert scale of 1-5. Depending on the student's response, the facilitator can probe for more information. A facilitator would then tally the total responses, identify any outlier responses, and analyze data and monitor progress to delineate next steps.

Using previous engagement methods, it took on average approximately ten minutes for student engagement with variable response times ranging from two to five minutes. However, upon introducing the disclosed system, student engagement was almost immediate. Results indicate that it consistently took less than one minute for a student to provide insightful and related feedback. Furthermore. students were engaged on average for more than 20 minutes, resulting in more than half of a counseling session. With this level of engagement, students were able to effectively provide a 3-fold increase in meaningful feedback. For example, in this study, using previous engagement methods an average of only 2.5 comments per session were recorded whereas using the disclosed system the average comments per session increased to 7.5. For example, when being shown the "sad" character, a student stated that the character was "alone." When asked about this, the student elaborated that he felt alone because he did not want to do what his friends wanted him to do, thus, not succumbing to peer pressure. This then allowed the School Psychologist to facilitate conversation regarding student's feelings and proposed solutions with similar situations. Using the disclosed system encouraged continued discussion across following sessions and indicated supporting, promising evidence that with this technology. students are able to increase their emotional responsiveness and expression with others.

Example 2 Clinical Study 2

This 6 week study using the disclosed method and system was part of a Positive Behavior Intervention and Supports System (PBIS), to survey all children regarding the social-emotional status and identify students at-risk and in need of intervention and support. The study group comprised a group of five second grade students, a group of six third grade students, a group of six fourth grade students and a group of two fifth grade students. Students were presented the primary assets/characters from the disclosed system. In this study the primary mode of presentation was a target object comprising either a three dimensional cube with unique fiducial marker on each of the six faces or a two dimensional index card with a unique fiducial marker located in each box of a 2×3 grid along with a computing device (e.g., a tablet and/or a smart phone) running the computer implemented system. The target object was placed on the table and the student was allowed to hold the computing device which was running the computer implemented system, enabling the student to view all 6 characters (Happy, Sad, Angry, Disgust, Fear, and Bored) simultaneously. After defining each character, a facilitator then prompted the student with a question, such as, e.g., "Think about how you've been feeling lately, which one would you say looks the way you feel." The student would then be allowed to interact with the screen of the computing device to select the character most accurately representing the student's emotion. After selection of an emotion, a student could then rate the degree of that emotion using a Likert scale of 1-5. Depending on the student's response, the facilitator can probe for more information. A facilitator would then tally the total responses, identify any outlier responses, and analyze data and monitor progress to delineate next steps.

Using previous engagement methods, it took on average approximately ten minutes for student engagement with variable response times ranging from two to five minutes. However, upon introducing the disclosed system, student engagement was almost immediate. Results indicate that it consistently took less than one minute for a student to provide insightful and related feedback. Furthermore. students were engaged lasted longer, with an average time lasting more than 20 minutes, resulting in more than half of a counseling session. With this level of engagement, faster and more in-depth assessment and behavioural analysis was achieved. In addition, using the disclosed method and system, students were able to provide a 3-fold increase in effectively and meaningful feedback. For example, in this study, using previous engagement methods an average of only 2.5 comments per session were recorded whereas using the disclosed system the average comments per session increased to 7.5.

Furthermore, the disclosed method and systems more quickly identified "at-risk" students within the first two weeks of the study versus previous methods which typically take 6-8 weeks to identify "at risk" students. As such, appropriate interventions and more intensive counseling support could be implemented much more quickly during instructional or unstructured time. For example, students were taught how to identify/express their emotions, the possible source of their emotion(s), and strategies to "calm down" when they experience the emotion. The results indicate that these "at risk" students exhibited a decrease in elevated emotional responses and improved communication by the end of six weeks.

In conclusion, this 6-week study demonstrated that using the disclosed method and system, there was an immediate engagement by students, the engagement resulted in significantly more and effective student feedback, resulting in a faster assessment of the student's emotional and social health. This engagement resulted in accurate assessment of a student in 1-2 weeks versus prior techniques which typically took 6-8 weeks. Such outcomes provided more effective behavioural therapy and counselling for the student, identified "at risk" students much faster that prior methods, and enabled faster implementation of appropriate intervention and counselling support.

The disclosed system can be used by School Psychologists, Speech Language Pathologists, Teachers. and Support Staff for all students in both elementary and secondary programs. Thus, the use of the disclosed system can enable student progress at a faster, more efficient rate, resulting in an overall decreased need for intervention.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc. for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as "comprise" and "comprises", and equivalent open-ended transitional phrases thereof like "including," "containing" and "having", encompasses all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents is based on the information available to the applicant and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method for objectively tracking and analyzing the social and emotional activity of a patient using a computing device, the method comprising the steps of:
    implementing an augmented reality tracking application in memory on the computing device;
    detecting by at least one camera a multi-faced target object manipulated by the patient, the multi-faced target object comprising at least one face, each of the at least one face comprising a computer-readable fiducial marker;
    displaying on a screen of the computing device at least a first set of augmented images or videos overlaid on the multi-faced target object, each of the first set of augmented images or videos being associated with one of the at least one face of the multi-faced target object, and wherein each of the at least first set of augmented images or videos is associating with a therapeutic subject;
    detecting a position and a rotation data relative to the camera of the multi-faced target object for each point in time; wherein the position and rotation data comprises one or more parameters indicative of the patient focusing attention on each of the at least first set of augmented images or videos, wherein the one or more parameters comprises the time each of the at least one face is in an upright orientation, the time each of the at least one face has a larger screen area, the amount of patient interaction associated with each of the at least one face, and the therapeutic subject associated with each of the at least first set of augmented images or videos;
    calculating a coordinate data set of the multi-faced target object based on the position and rotation data detected;
    determining an active face for each point in time using the coordinate data set, wherein the active face can be dynamically assigned to each of the at least one face at each point in time and; and
    storing as a data set the position and rotation data, the coordinate data set, the active face, and a time for each point in time.

2. The method of claim 1, wherein the therapeutic subject comprises a module on emotion identification, a module on abstract language, a module on social skills, and/or a module on emotional quotient.

3. The method of claim 2, wherein the module on emotion identification comprises the emotions happy, sad, angry, fear, bored and/or disgusted.

4. The method of claim 1, further comprising the steps of:
    displaying on a screen of the computing device at least second set of augmented images or videos in place of displaying the at least first set of augmented images or videos upon receiving an input activating a first image link associated with each of the at least first set of augmented images or videos, each of the at least second set of augmented images or videos being associated with one of the at least one face of the multi-faced target object, wherein each of the at least second set of augmented images or videos is different than the one associated with the each of the at least first set of augmented images or videos, and wherein each of the at least second set of augmented images or videos is associating with a therapeutic subtopic; the therapeutic subtopic providing additional information on the therapeutic subject associated with that therapeutic subtopic; and determining, for the second set of augmented images or videos, an active face for each point in time using the coordinate data set, wherein the active face can be dynamically assigned to each of the at least one face at each point in time, and wherein the one or more parameters further comprises the therapeutic subtopic associated with each of the at least second set of augmented images or videos.

5. The method of claim 4, wherein the therapeutic subtopic of the therapeutic subject for a module on emotion identification comprises:

a happy therapeutic subtopic comprises being joyful, being happy over an individual success, being happy over a team success, being congratulated by parents, being congratulated by friends, and/or receiving physical love;

a sad therapeutic subtopic comprises suffering a personal loss, suffering a family loss, suffering a tangible loss, being neglected, being harassed or bullied, being alone, and/or low self-image and self-reflection;

an angry therapeutic subtopic comprises fighting with others, lashing out, an internal tantrum, an external tantrum, a jealousy, and/or a loss;

a fear therapeutic subtopic comprises an external fear of objects, an anxiety or worry in a social situation, an internal fear, an external non-real fear, a real conflict, and/or a fear of physical danger;

a bored therapeutic subtopic comprises being alone, uninterested or lacking responsiveness with others, uninterested or lacking responsiveness with objects, uninterested or lacking responsiveness in school, uninterested or lacking responsiveness in playing, uninterested or lacking responsiveness with a chore, indifferent an authority figure, indifferent to affection; and/or a disgusted therapeutic subtopic comprises being physically sick due to external stimulus, having a perceived sickness due to an external stimulus, smelling stinky laundry, smelling skunk odor, smelling garbage, stepping on gum, having dirty hands, and/or disgust with littering.

6. The method of claim 1, wherein each of the at least first set of augmented images or videos overlaid on the multi-faced target object is displaying on a screen of the computing device even when the face associated with that augmented image or video is out of view of the at least one camera.

7. The method of claim 1 further comprising the steps of retrieving from memory one or more talking prompts associated with the therapeutic subject associated with each of the at least first set of augmented images or videos; and communicating the one or more talking prompts through a second computing device to a user.

8. The method of claim 1 further comprising the steps of transmitting the data set to a second computing device; and displaying to a user at least a portion of the data set on a second screen of the second computing device.

9. The method of claim 8 further comprising the steps of collecting video and/or audio recordings a of the patient; transmitting the video and/or audio recordings to the second computing device; and playing the video and/or audio recordings on the second screen of the second computing device.

10. The method of claim 8 further comprising the steps of transmitting a mirror video and/or audio recording of the screen of the first computing device to the second computing device; and playing the mirror video and/or audio recording on the second screen of the second computing device.

11. The method of claim 8 further comprising the steps of establishing a videotelephony session between the patient and the user to permit the transmission in real-time and audio-video signal.

12. The method of claim 8 further comprising the steps of processing the data set to automatically create a graphical representation of the data set; and displaying the graphical representation on the second screen of the second computing device.

13. The method of claim 1, wherein the at least one face of the multi-faced target object comprises a first face and a second face, the first face comprising a first computer-readable fiducial marker and the second face comprising a second computer-readable fiducial marker, the at least first set of augmented images or videos comprise a first augmented image associated with the first fiducial marker and a second augmented image or video associated with the second fiducial marker, wherein the first augmented image is associated with a first therapeutic subject, the second augmented image is associated with a second therapeutic subject, and the one or more parameters further comprises the first therapeutic subject and the second therapeutic subject.

14. The method of claim 13, wherein the at least one face of the multi-faced target object further comprises a third face, the third face comprising a third computer-readable fiducial marker and the at least first set of augmented images or videos overlaid on the multi-faced target object further comprise a third augmented image associated with the third fiducial marker, wherein the third augmented image is associated with a third therapeutic subject and the one or more parameters further comprising the third therapeutic subject.

15. The method of claim 14, wherein the at least one face of the multi-faced target object further comprises a fourth face, the fourth face comprising a fourth computer-readable fiducial marker and the at least first set of augmented images or videos overlaid on the multi-faced target object further comprise a fourth augmented image associated with the fourth fiducial marker, wherein the fourth augmented image is associated with a fourth therapeutic subject and the one or more parameters further comprising the fourth therapeutic subject.

16. The method of claim 15, wherein the at least one face of the multi-faced target object further comprises a fifth face, the fifth face comprising a fifth computer-readable fiducial marker and the at least first set of augmented images or videos overlaid on the multi-faced target object further comprise a fifth augmented image associated with the fifth fiducial marker, wherein the fifth augmented image is associated with a fifth therapeutic subject and the one or more parameters further comprising the fifth therapeutic subject.

17. The method of claim 16, wherein the at least one face of the multi-faced target object further comprises a sixth face, the sixth face comprising a sixth computer-readable fiducial marker and the at least first set of augmented images or videos overlaid on the multi-faced target object further comprise a sixth augmented image associated with the sixth fiducial marker, wherein the sixth augmented image is associated with a sixth therapeutic subject and the one or more parameters further comprising the sixth therapeutic subject.

\* \* \* \* \*